(12) United States Patent
Chan et al.

(10) Patent No.: US 11,804,120 B2
(45) Date of Patent: Oct. 31, 2023

(54) BABY MONITOR SYSTEM WITH MULTIPLE AUDIO FEATURE

(71) Applicant: Merit Zone Limited, Hong Kong (CN)

(72) Inventors: Kelvin Ka Fai Chan, Hong Kong (CN); Hon Hung Leung, Hong Kong (CN); Hon Kuen Chan, Hong Kong (CN); Zhi Qiang Gan, Hong Kong (CN); Tse Yim Lau, Hong Kong (CN)

(73) Assignee: Merit Zone Limited, Hong Kong (CN)

( * ) Notice: Subject to any disclaimer, the term of this patent is extended or adjusted under 35 U.S.C. 154(b) by 94 days.

(21) Appl. No.: 17/648,554

(22) Filed: Jan. 21, 2022

(65) Prior Publication Data

US 2022/0238000 A1 Jul. 28, 2022

Related U.S. Application Data

(60) Provisional application No. 63/142,005, filed on Jan. 27, 2021.

(51) Int. Cl.
| | | |
|---|---|---|
| *G08B 21/02* | (2006.01) | |
| *H04N 7/18* | (2006.01) | |
| *A61B 5/0205* | (2006.01) | |
| *G08B 13/196* | (2006.01) | |

(52) U.S. Cl.
CPC ...... *G08B 21/0208* (2013.01); *A61B 5/02055* (2013.01); *G08B 13/19684* (2013.01); *H04N 7/181* (2013.01)

(58) Field of Classification Search
CPC .......... G08B 21/0208; G08B 13/19684; A61B 5/02055; A61B 2503/04; A61B 5/0077; A61B 5/1113; A61B 5/1128; H04N 7/181; H04N 7/185
See application file for complete search history.

(56) References Cited

U.S. PATENT DOCUMENTS

| | | | | |
|---|---|---|---|---|
| 7,151,444 B1* | 12/2006 | Doyle | ................ | G08B 21/0208 340/815.4 |
| 2006/0232428 A1* | 10/2006 | Desrosiers | ............. | G08B 21/02 340/539.15 |
| 2007/0236344 A1* | 10/2007 | Desrosiers | ......... | G08B 21/0227 340/539.15 |
| 2008/0077020 A1* | 3/2008 | Young | .................... | A61B 5/746 73/726 |
| 2010/0109878 A1* | 5/2010 | Desrosiers | ............. | H04N 7/185 340/573.4 |

(Continued)

*Primary Examiner* — Ryan W Sherwin
(74) *Attorney, Agent, or Firm* — S&F/WEHRW

(57) ABSTRACT

A monitor system with dual audio or multiple audio feature for simultaneously monitoring one or more target subjects is disclosed. The monitor system includes a plurality of camera devices and a base station. The plurality of camera devices is arranged to capture video data and sound data of the one or more target subjects independently and simultaneously. The base station is configured to receive the video data and the sound data from the plurality of camera devices, and present the video data and the sound data uninterruptedly. The base station comprises a display panel partitioned into a plurality of regions for displaying multiple views simultaneously using a split-screen technique. The base station outputs an audio signal by combining the sound data from the plurality of camera devices into a single audio signal.

21 Claims, 8 Drawing Sheets

(56) References Cited

U.S. PATENT DOCUMENTS

| | | | |
|---|---|---|---|
| 2011/0102174 A1* | 5/2011 | Pace | G08B 21/0208 |
| | | | 340/539.15 |
| 2017/0104963 A1* | 4/2017 | Veneziano | H04N 7/183 |
| 2019/0020530 A1* | 1/2019 | Au | H04W 72/21 |
| 2019/0205655 A1* | 7/2019 | Matsuoka | G06V 20/52 |

* cited by examiner

BABY MONITOR SYSTEM WITH MULTIPLE AUDIO FEATURE

CROSS-REFERENCE TO RELATED APPLICATIONS

This application claims the benefit of the U.S. Provisional Patent Application No. 63/142,005, filed on Jan. 27, 2021, which is incorporated by reference herein in its entirety.

FIELD OF THE INVENTION

The present disclosure generally relates to the technical field of baby monitors. In particular, the present disclosure relates to a monitor system with dual audio or multiple audio feature for simultaneously monitoring one or more target subjects.

BACKGROUND OF THE INVENTION

Baby monitor is a very popular electronic consumer product for parents or caretakers to monitor the condition of a baby from afar. Such a system includes a camera device and a monitor device paired together such that they can be connected wirelessly. The camera device is placed nearby a baby (or other target subjects) for detecting voice and movement made by the baby and capturing sounds and/or images. The captured sounds and/or images are encrypted and transmitted to the monitor device, which presents the sounds and images for monitoring purposes by the parents or the caretakers.

For families with more than one baby, the parents will normally buy more camera devices for monitoring all the babies at the same time. To facilitate the user to monitor, the baby monitor device may have a split-screen viewing feature to allow parents to view both feeds together on one screen. However, the split-screen viewing feature can allow simultaneously video streaming from paired camera devices, but this is not applicable for audio data. On the contrary, the audio data from paired camera devices can only be broadcasted sequentially or selectively at different time slots. For example, the audio data from the first camera device can be heard in the first 15 seconds, and then the audio data from the second camera device can be heard in the next 15 seconds, and this sequence repeats again and again. The drawback of this approach is that some voices may be missed if that camera device is in the non-activated time slot.

Accordingly, there is a need in the art to have a baby monitor system with two or more camera devices that is capable of outputting audio signals from the two or more camera devices simultaneously. Furthermore, other desirable features and characteristics will become apparent from the subsequent detailed description and the appended claims, taken in conjunction with the accompanying drawings and this background of the disclosure.

SUMMARY OF THE INVENTION

In the light of the foregoing background, it is an objective of the present disclosure to provide a monitor system with two or more camera devices that is capable of for monitoring one or more target subjects simultaneously.

In accordance with the first embodiment of the present disclosure, the monitor system includes a plurality of camera devices and a base station. The plurality of camera devices is arranged to capture video data and sound data of the one or more target subjects independently and simultaneously. The base station is configured to receive the video data and the sound data from the plurality of camera devices, and present the video data and the sound data uninterruptedly. The base station includes a display panel partitioned into a plurality of regions for displaying multiple views simultaneously using a split-screen technique. The base station outputs an audio signal by combining the sound data from the plurality of camera devices into a single audio signal.

In accordance with a further aspect of the present disclosure, the base station includes an amplifier and a base processor. The base processor is configured to decode the sound data and the video data, add or combine the sound data from the plurality of camera devices to obtain the single audio signal, and transmit the single audio signal to the amplifier.

In accordance with a further aspect of the present disclosure, an individual camera device includes a sound capture circuitry comprising a microphone for acquiring the sound data of the target subject, a video capture circuitry provided in a camera assembly for acquiring the video data of the target subject, and a camera processor configured to generate a data packet comprising a header and a payload data, wherein the header includes a pairing identity (ID) for identifying the individual camera device, and wherein the payload data includes the sound data, the video data, and a temperature reading captured by the individual camera device.

In accordance with a further aspect of the present disclosure, the camera processor is further configured to scale down the video data before generating the data packet for reducing a transmission time of the data packet from the individual camera device to the base station.

In accordance with a further aspect of the present disclosure, the base processor is configured to receive the data packets from the plurality of camera devices and process the data packets sequentially and continuously.

Preferably, the plurality of camera devices transmits the data packet to the base station during a first frame, and the base station presents information from the data packet during a second frame.

In certain embodiments, the camera processor is further configured to nullify the sound data when generating the data packet if the individual camera device is muted or the sound data has a volume less than a pre-determined level for reducing a transmission time of the data packet from the individual camera device to the base station.

In accordance with a further aspect of the present disclosure, the camera assembly includes a sensor module, one or more optical elements, one or more infrared (IR) light-emitting diodes (LEDs), and a photosensitive diode.

In accordance with a further aspect of the present disclosure, the sound data is encoded using a μ-Law algorithm or an A-Law algorithm.

In accordance with a further aspect of the present disclosure, the video data is encoded using an advanced video coding (AVC) codec.

In accordance with a further aspect of the present disclosure, the plurality of camera devices is wirelessly connected to the base station using radio frequency (RF) signals.

In accordance with the second embodiment of the present disclosure, a monitor system for simultaneously monitoring one or more target subjects using a series of time frames is disclosed. The series of time frames are pre-determined in frame periods. The monitor system includes a plurality of heterogeneous sources arranged to monitor the one or more target subjects independently and simultaneously, and transmit a data packet to the base station during a first frame of the series of time frames, and a base station configured to receive the data packet from the plurality of heterogeneous sources, and presents information from the data packet during a second frame of the series of time frames. The data packet includes a header for identifying an individual heterogeneous source and a payload data obtained by the individual heterogeneous source. The payload data from the plurality of heterogeneous sources are displayed or output from the base station during the second frame simultaneously.

In accordance with a further aspect of the present disclosure, the plurality of heterogeneous sources includes one or more detectors selected from the group consisting of a camera device, a heartbeat sensor, a proximity sensor, a temperature sensor, and a hall-effect sensor. The temperature sensor and the heat beat sensor are configured to obtain vitals of the target subject. The hall-effect sensor is installed on a children's safety product for confirming whether the children's safety product is properly secured or closed.

In accordance with a further aspect of the present disclosure, the individual heterogeneous source includes a processor configured to generate the data packet, wherein the header includes a pairing identity (ID).

In accordance with a further aspect of the present disclosure, the base station is capable of simultaneously and independently presenting multiple views from the plurality of heterogeneous sources using a split-screen technique.

In accordance with a further aspect of the present disclosure, the base station is capable of producing an audio output from sound data captured from the plurality of heterogeneous sources.

In one embodiment, the plurality of heterogeneous sources and the base station each include a phase lock loop circuit configured to define a synchronized frequency for handling the data packets.

In an alternative embodiment, the plurality of heterogeneous sources and the base station each include a phase lock loop circuit configured to define a non-synchronized frequency for handling the data packets, and wherein the base station is configured to present updated information when a new content is received at a starting time of the second frame.

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which.

DETAILED DESCRIPTION OF THE INVENTION

Figure 1:
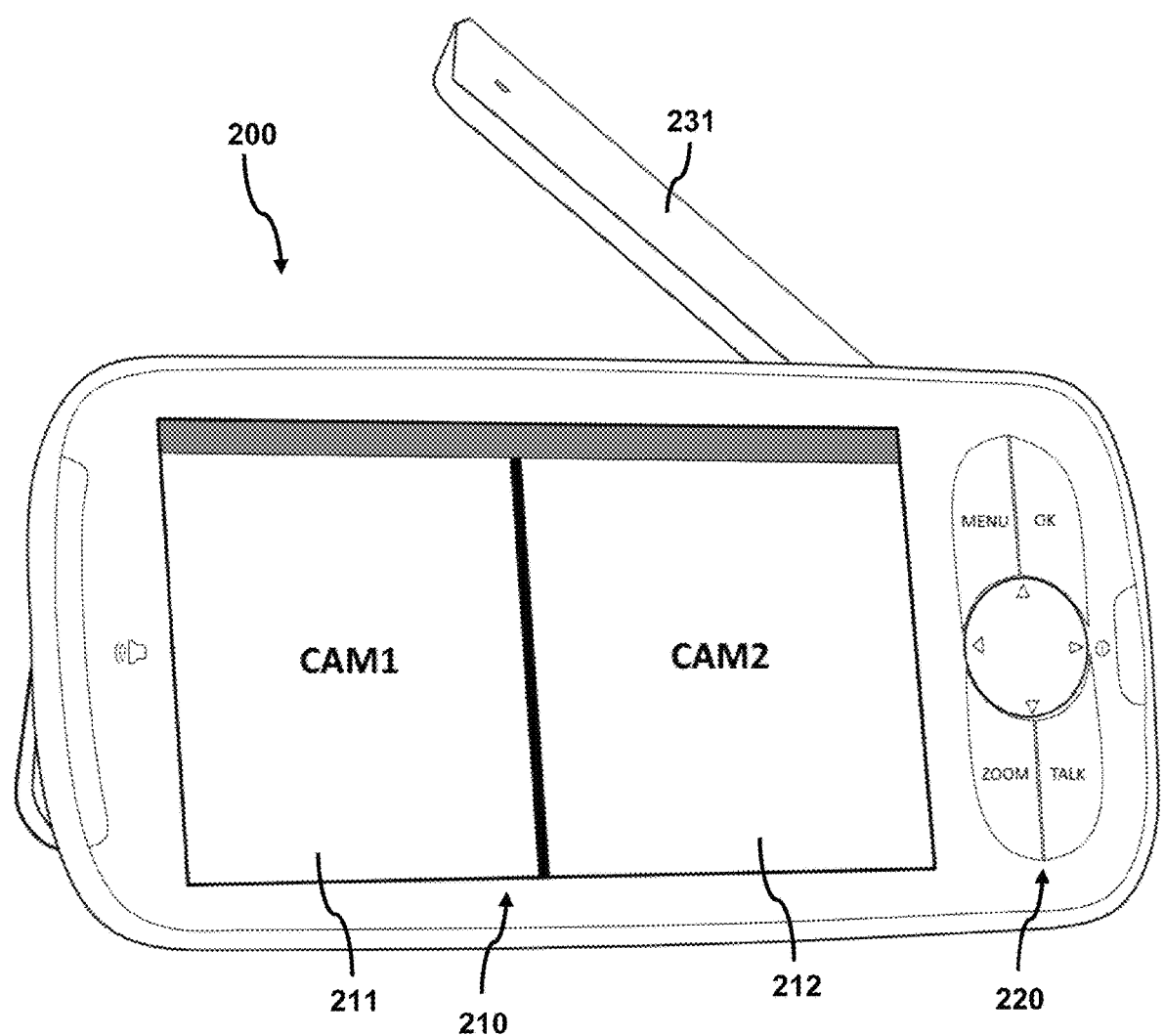
FIG. 1 illustrates a base station in accordance with certain embodiments of the present disclosure.

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The benefits, advantages, solutions to problems, and any element(s) that may cause any benefit, advantage, or solution to occur or become more pronounced are not to be construed as a critical, required, or essential features or elements of any or all of the claims. The invention is defined solely by the appended claims including any amendments made during the pendency of this application and all equivalents of those claims as issued.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The use of any and all examples, or exemplary language (e.g., "such as") provided herein, is intended merely to illuminate the invention better and does not pose a limitation on the scope of the invention unless the claims expressly state otherwise. Terms such as "first", "second", and the like are used herein to describe various elements, components, regions, sections, etc., and are not intended to be limiting. Recitation of ranges of values herein is merely intended to serve as a shorthand method of referring individually to each separate value falling within the range, unless otherwise indicated herein, and each separate value is incorporated into the specification as if it were individually recited herein. No language in the specification should be construed as indicating any non-claimed element as essential to the practice of the invention.

The term "processor", as used herein, is intended to include any integrated circuit or other electronic device or devices capable of performing an operation of at least one instruction. The processor includes, but is not limited to, microcontroller unit (MCU), central processing unit (CPU), digital signal processor (DSP), microprocessor, multi-core processor, and the like.

The term "target subject", as used herein, may refer to a subject for which the monitor system is used to monitor, and the subject may be an animal, a human being (baby, toddler, elderly), or other non-biological subject, such as a vehicle, a boat, and so on.

Unless defined otherwise, all technical and scientific terms used herein in the specification shall have the same meaning as commonly understood by one of ordinary skill in the art to which the present invention belongs.

In light of the background and the problem stated therein, the present invention is disclosed to provide a monitor system with two or more camera devices that is capable of outputting audio signals from the two or more camera devices simultaneously.

FIG. 1 illustrates an exemplary embodiment of a base station 200 capable of simultaneously and independently presenting multiple views from a plurality of heterogeneous sources, and producing an audio output from sounds captured from the plurality of heterogeneous sources. The multiple views are presented using a split-screen technique on the display panel 210. In the illustrated embodiment, the display panel 210 is partitioned into two regions 211, 212 and the two views from two heterogeneous sources are simultaneously and independently presented on the first region 211 and the second region 212 respectively. It is apparent that the display panel 210 may support partition into multiple regions for presenting the views and information from multiple heterogeneous sources without departing from the scope and spirit of the present disclosure. It is also apparent that the display panel 210 can also present one single view with or without partition. Optionally and preferably, the base station 200 also includes a mode interface 220 and an antenna 231.

Figure 2:
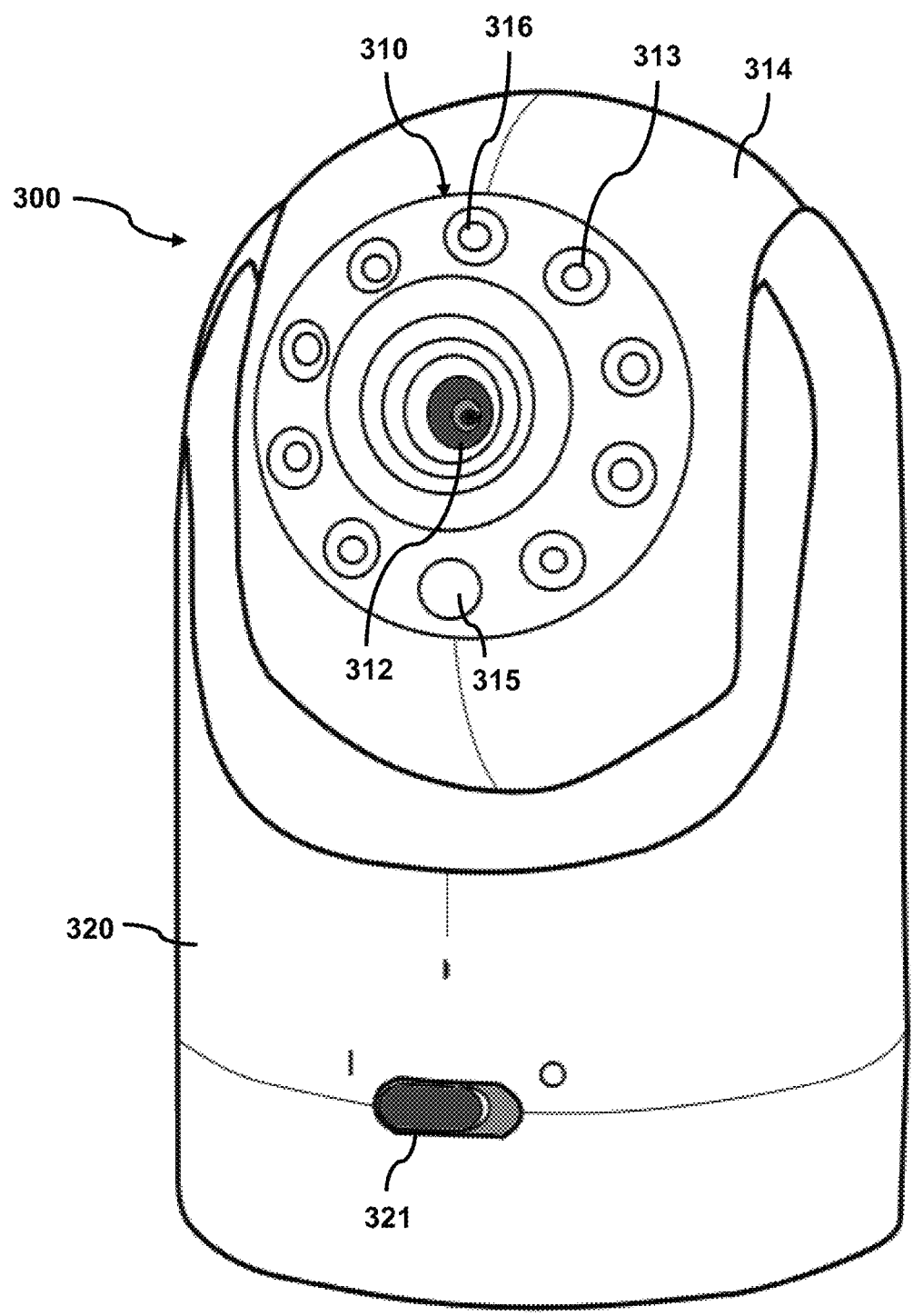
FIG. 2 illustrates a camera device in accordance with certain embodiments of the present disclosure.

FIG. 2 illustrates an exemplary embodiment of a camera device 300 for capturing images and/or videos of a target subject, such as a baby. In one embodiment as illustrated, the camera device 300 comprises a base 320 and a camera assembly 310 mounted on the base 320 for capturing a video data. On the base 320, a microphone 330 (refer to FIG. 4) is incorporated into the camera device 300 for capturing a sound data. On the front part of the base 320, there is also provided with a main switch 321 for toggling between on and off, and optionally other buttons and status indicators. Although the base 320 in the illustrated embodiment is cylinder in shape for supporting the camera assembly 310, it is apparent that the base 320 may have other shapes without departing from the scope and spirit of the present disclosure. In particular, the camera device 300 may comprise a clamp, an arm, a pivot support, or other mechanical structures for mounting on a wall or a crib.

The camera assembly 310 is provided in a camera housing 314, which is rotatable in at least one dimension about the base 320 for panning the camera assembly 310. The camera housing 314 is in a spherical shape for easing the rotation of the camera assembly 310. The camera assembly 310 includes a sensor module 311 (refer to FIG. 4), one or more optical elements 312, one or more infrared (IR) light-emitting diodes (LEDs) 313, a power LED 315 and a photosensitive diode 316. As in other conventional designs, the photosensitive diode 316 is configured to detect the intensity of light for determining whether the target subject in a low light intensity environment. The power LED 315 is an indicator showing the status of the camera device 300. The one or more optical elements 312 are arranged to realize beam-shaping to the sensor module 311, which may include mirrors, lens, zoom lens, beam splitter, collimator, other optical devices, or any combinations thereof.

Figure 3:
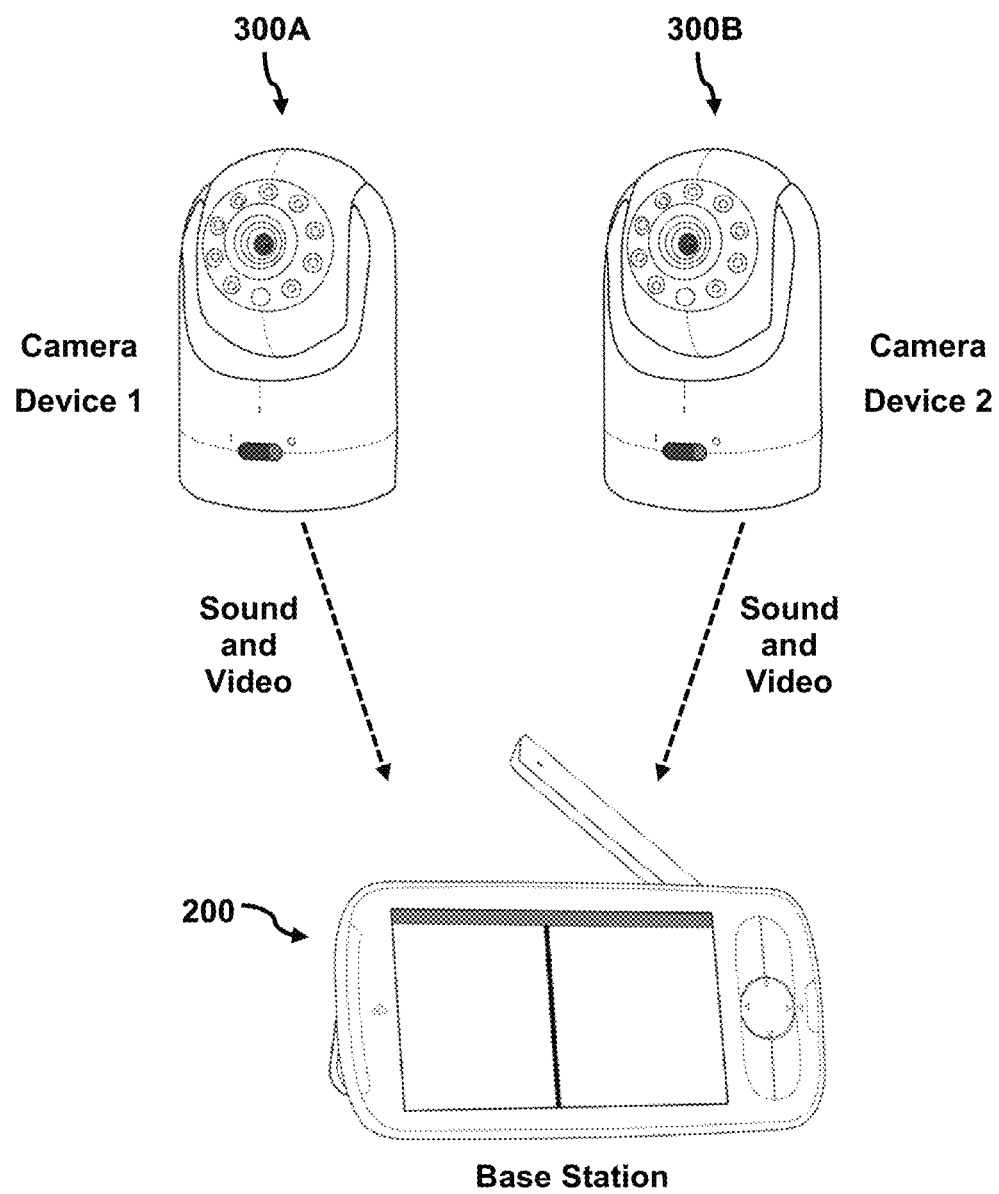
FIG. 3 illustrates a monitor system having two camera devices in accordance with certain embodiments of the present disclosure.

FIG. 3 depicts a monitor system 100 for monitoring one or more target subjects in accordance with a preferred embodiment of the present disclosure. The monitor system 100 comprises the base station 200 of FIG. 1, wirelessly connected to two heterogeneous sources, which are both camera devices 300 of FIG. 2 arranged to monitor one or more target subjects independently and simultaneously. For simplicity and identification purposes, the first camera device is denoted as 300A, and the second camera device is denoted as 300B. The two heterogeneous sources are arranged to monitor two target subjects, for example, two children, independently and simultaneously. The base station 200 is configured to receive video data and sound data from the two camera devices 300 for monitoring each target subject, and present the video data and the sound data uninterruptedly. Particularly, the base station 200 is capable of producing an audio output from sound data captured from the two camera devices 300.

In certain embodiments, the heterogeneous sources may not necessarily be camera devices 300, instead, the heterogeneous sources may include one or more detectors selected from the group consisting of a heartbeat sensor, a proximity sensor, a temperature sensor, a hall-effect sensor, and the like. For example, the temperature sensor and the heat beat sensor may be used to obtain vitals (body temperature and pulse rate) from the baby for determining the health condition of the baby, in particular, the temperature sensor and the heat beat sensor may be incorporated in a wearable device. The hall-effect sensor may be installed on children's safety products, such as baby cribs and baby gates, for confirming whether the children's safety product is properly secured or closed.

In the illustrated embodiment, the first camera device 300A and the second camera device 300B are arranged to capture sound data and video data of two target subjects. Though the first camera device 300A and the second camera device 300B are shown to be wirelessly connected directly to the base station 200, the communication may be otherwise using a wired connection without departing from the scope and spirit of the present disclosure. The sound data and video data captured by the camera device 300 are transmitted to the base station 200 directly using radio frequency (RF) signal, including but not limited to 2.4 GHz Frequency-hopping spread spectrum (FHSS), Bluetooth, Zigbee, Digital Addressable Lighting Interface (DALI), or indirectly using Wi-Fi network, cellular, low power wide area network (LPWAN), or other suitable technologies known in the art, or any combinations thereof.

Figure 4:
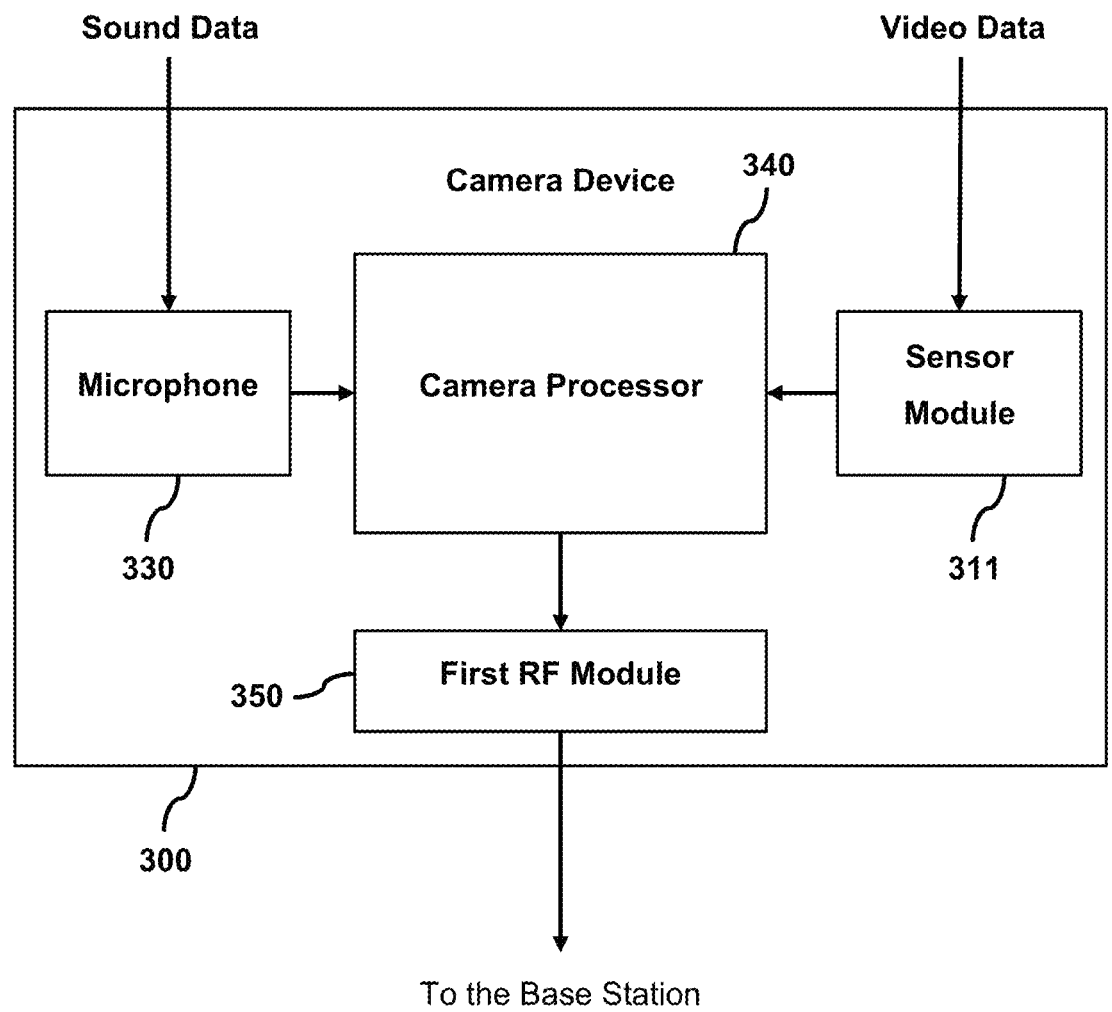
FIG. 4 is a block diagram of the camera device in accordance with certain embodiments of the present disclosure.

FIG. 4 shows a block diagram of the camera device 300 according to an embodiment of the present invention. The camera device 300 comprises a sound capture circuitry having a microphone 330, a video capture circuitry having a sensor module 311, a camera processor 340, and a first RF module 350. The microphone 330 is configured to capture sound data of the target subject, and the sensor module 311 is a complementary metal-oxide-semiconductor (CMOS) sensor configured to capture video data of the target subject. The camera processor 340 is configured to receive the sound data and video data at the same time from the sound capture circuitry and the video capture circuitry respectively. The camera processor 340 is configured to generate a data packet for transmitting the sound and video data to the first RF module 350. The camera processor 340 is further configured to scale down the video data for reducing a transmission time from the camera device 300 to the base station 200. The first RF module 350 transmits the packets to the base station 200 using RF signals for further processing and storage. In particular, the RF module 350 is configured to perform point-to-point (P2P) direct communication with the base station 200. Unlike other security surveillance cameras, the communication does not go through the Internet and the packets are not transmitted to a server or a network database. In one preferred embodiment, the camera device 300 communicates with the base station 200 using 2.4 GHz FHSS, Bluetooth, Wi-Fi Direct, or other P2P communication over a network without the need of a wireless access point.

Figure 5:
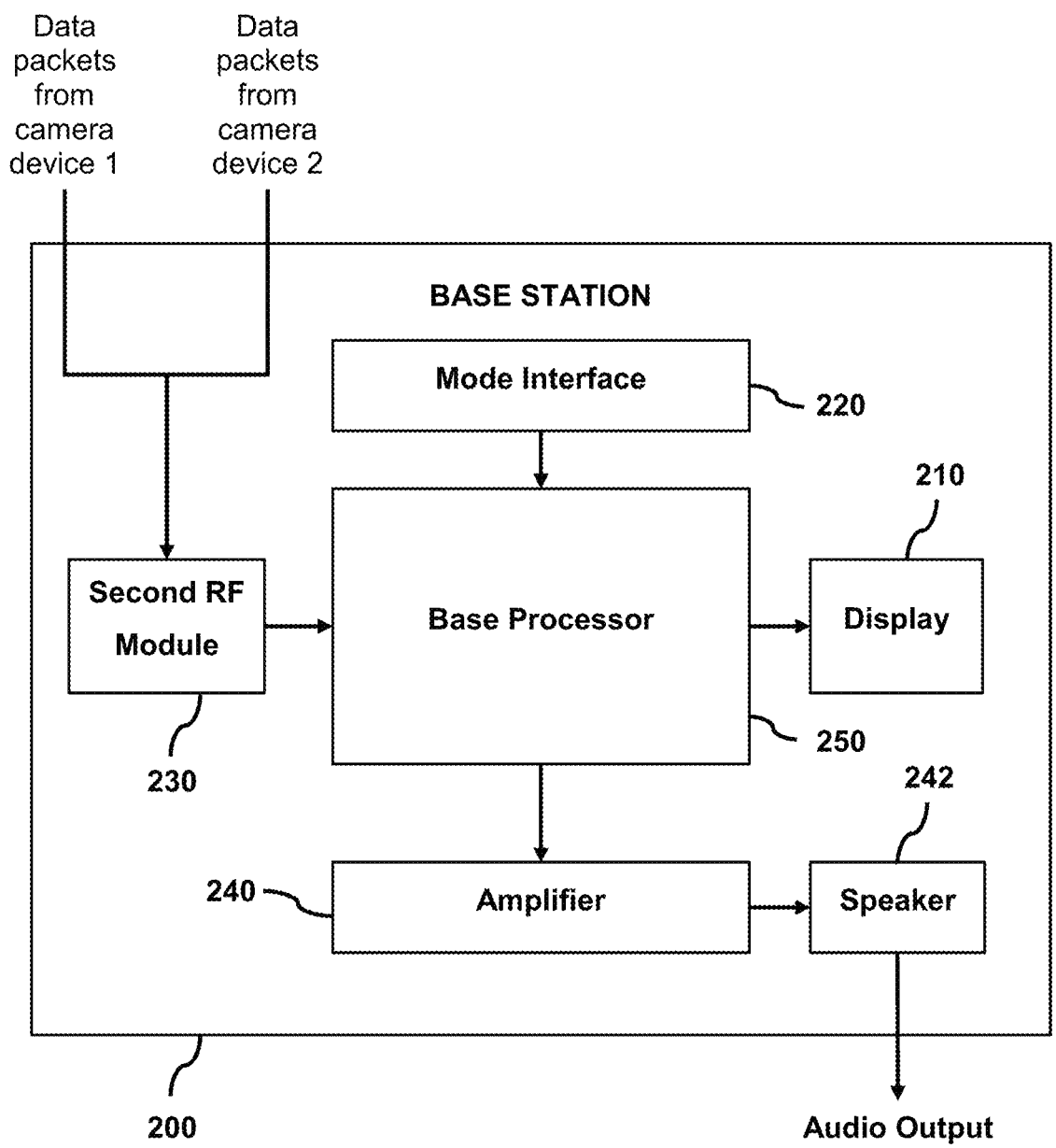
FIG. 5 is a block diagram of the base station in accordance with certain embodiments of the present disclosure.

FIG. 5 shows a block diagram of the base station 200 according to an embodiment of the present invention. The base station 200 comprises a base processor 250, a second RF module 230, a display 210, a mode interface 220, a speaker 242, and an amplifier 240. The base station 200 has the advantage of presenting the video data and the sound data continuously and uninterruptedly. When the data packets from the camera devices 300 are received by the second RF module 230 from the first RF module 350, the data packets are transmitted to the base processor 250 for processing. The base processor 250 is configured to decode the sound data and the video data using the corresponding codec, then add or combine all the sound data from the plurality of camera devices to obtain the single audio signal, and transmit the single audio signal to the amplifier 240. The mode interface 220 allows the parents or the caretakers to control the base station 200 and the plurality of camera devices 300 by selecting different modes of operations.

Figure 6:
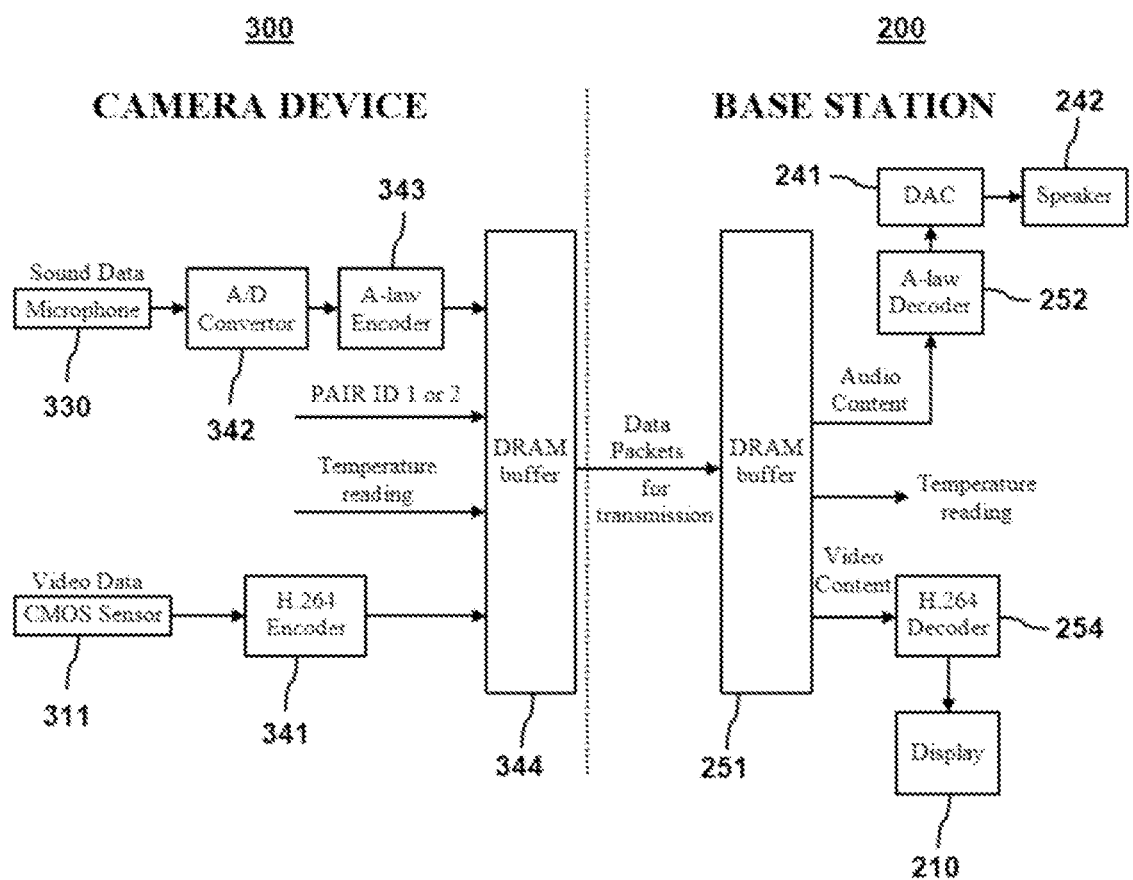
FIG. 6 is a flow chart illustrating the transmission of sound and video data from the camera devices to the base station in accordance with certain embodiments of the present disclosure.
Figure 7:
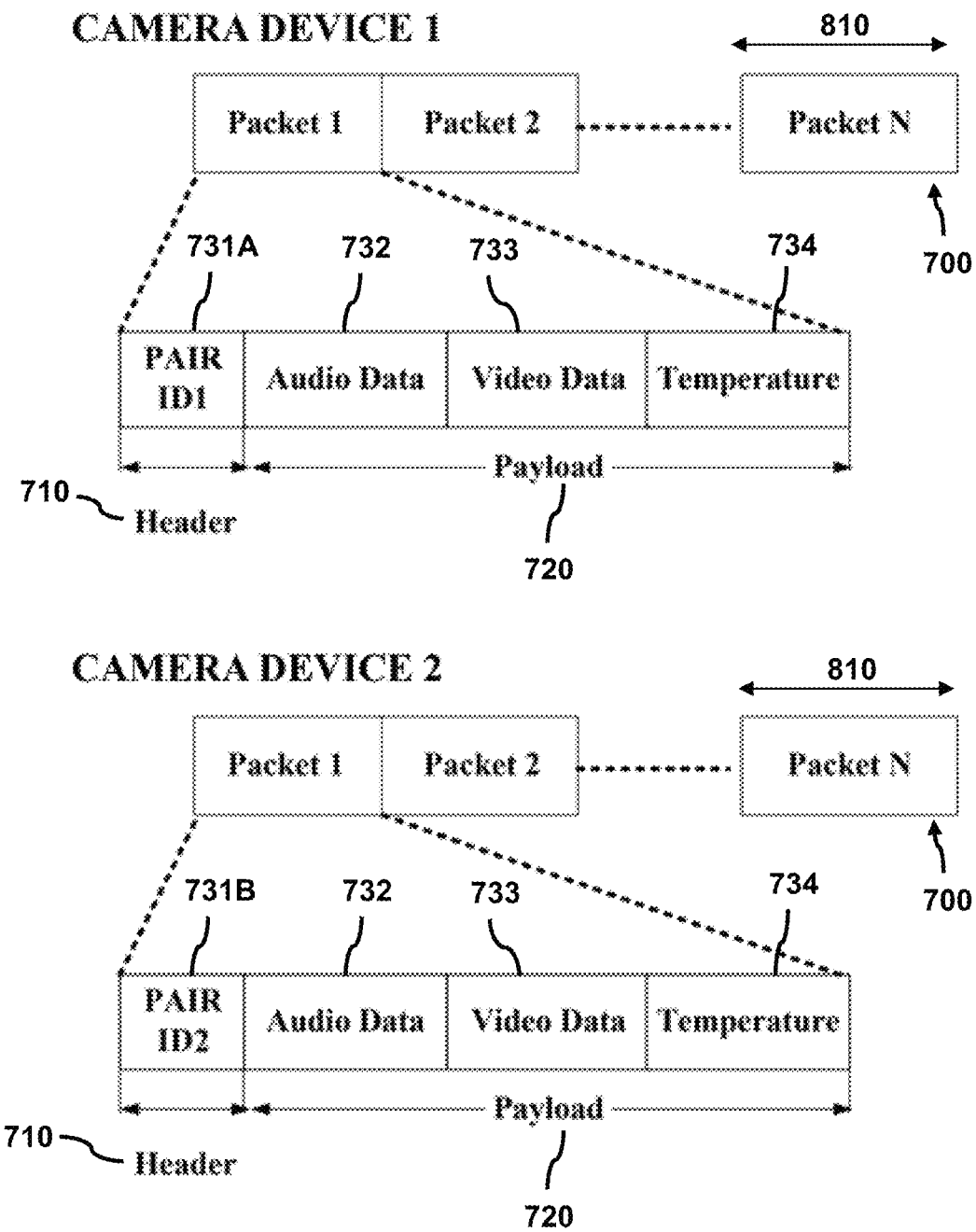
FIG. 7 is a diagram illustrating the data packets for transmitting information from the camera devices to the base station in accordance with certain embodiments of the present disclosure.

In further detail, FIG. 6 shows a flow chart illustrating the transmission of sound and video data from the camera devices 300 to the base station 200 in accordance with certain embodiments of the present disclosure. When the sound is captured by the microphone 330 of the camera device 300, the analog signal from the microphone is converted into a digital signal by the analog-to-digital converter 342. The sound data is then encoded by a sound encoder 343 using a μ-Law algorithm or an A-Law algorithm, and transmitted to a Dynamic random-access memory (DRAM) buffer 344. Similarly, for the video captured by the camera assembly 310, the video data is obtained by the sensor module 311, and subsequently encoded by a video encoder 341 using an advanced video coding (AVC) codec, such as H.264. The encoded signal is then transmitted to the DRAM buffer 344. The camera processor 340 is configured to obtain the video data and the sound data from the DRAM buffer 344, together with a pairing identity (ID) and other parameters such as temperature reading, and generate data packets for transmission by the first RF module 350. The structure of the data packet for transmission is shown in FIG. 7. On the base station 200, the data packets are received by the second RF module 230, and transmitted to the DRAM buffer 251 of the base station 200, in which the received data packets are combined. The base processor 250 is configured to collect the data packets from the DRAM buffer 251, for which the data packets are segmented to retrieve the audio content, the video content, and other information such as the temperature reading. The audio content is then decoded by a sound decoder 252 using the corresponding algorithm (the μ-Law algorithm or the A-Law algorithm). The sound data is transmitted to the amplifier 240 comprising a digital-to-analog converter 241, and outputted from the speaker 242.

The video content is decoded by a video decoder 254 using the respective codec, and the video data is then displayed on the display panel 210. The video data from different camera devices 300 are displayed in different regions. For the case of two camera devices 300, the first region 211 can display the video data from the first camera device 300A, and the second region 212 can display the video data from the second camera device 300B. Similar approach can be applied to the monitor system 100 having more than two camera devices 300.

Figure 8:
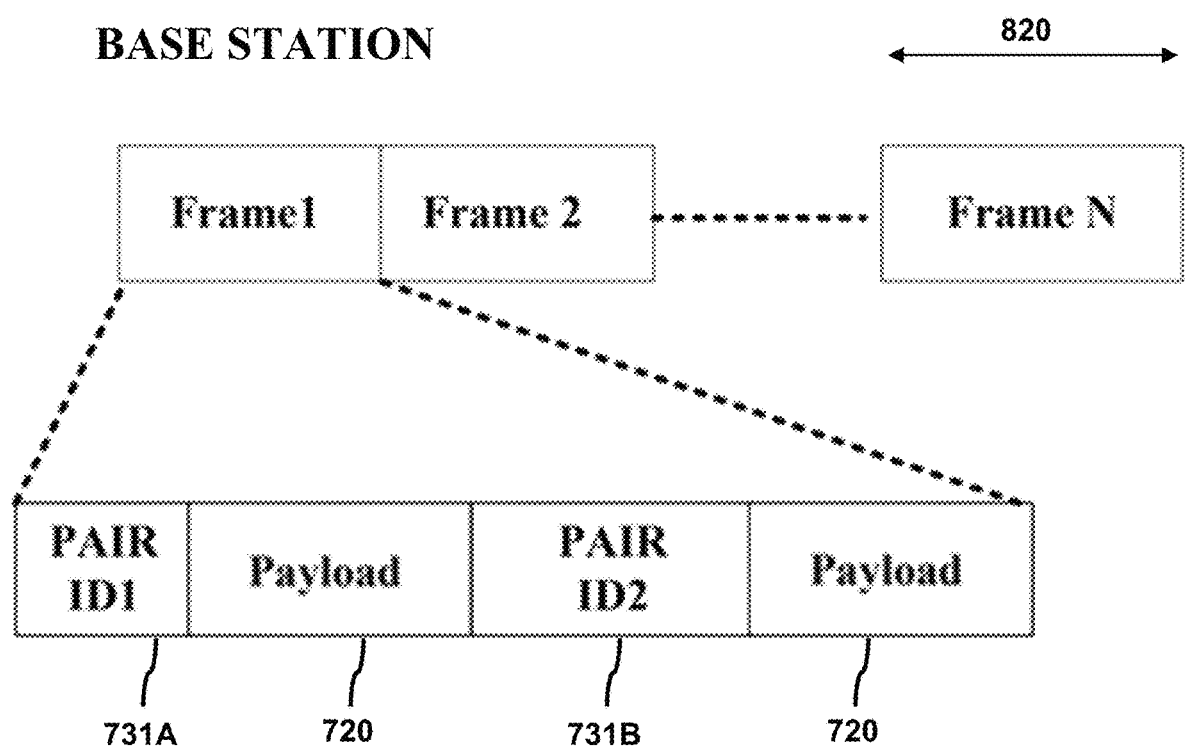
FIG. 8 is a diagram illustrating the time frames of the base station in accordance with certain embodiments of the present disclosure.

Another embodiment of the present disclosure provides a transmission of the monitor system 100 for sending data packets between the plurality of heterogeneous sources, particularly the camera devices 300, and the base station 200. The structure of the data packets of the camera devices 300 is shown in FIG. 7. The camera device 300 uses a series of time frames for transmitting the data packets 700. The series of time frames are pre-determined in frame periods. In each time frame, a data packet 700 is transmitted. The data packet 700 comprises a header 710 and a payload data 720. In certain embodiment, the header 710 comprises a pairing identity (ID) 731A for identifying the individual camera device. The payload data 720 comprises the audio data 732, the video data 733, and a temperature reading 734 captured by the individual camera device. It is apparent that the payload data 720 may include other information without departing from the scope and spirit of the present disclosure. When the monitor system 100 includes two camera devices 300, the second camera device 300B transmits a data packet 700 with a different pairing ID 731B, as the pairing ID 731A, 731B are used for identifying the individual camera device 300. The data packet 700 is transmitted to the base station 200 by the first RF module 350 during the first frame 810 of the series of time frames. The base station 200 receives the data packet 700 from the plurality of camera devices 300, and presents the information from the data packet 700 during a second frame 820 of the series of time frames. As illustrated in FIG. 8, the received data packet is processed during the second frame 820, in which the data packet 700 from the first camera device 300A and the data packet 700 from the second camera device 300B are combined in the DRAM buffer 251 as a single audio channel and processed sequentially and continuously. In the illustrated embodiment, the information processed during the second frame 820 includes the pairing ID 731A and the payload data 720 from the first camera device 300A, and the pairing ID 731B and the payload data 720 from the second camera device 300B. Particularly, the sound data from the first camera device 300A and the second camera device 300B are added or combined to obtain a single audio signal. The single audio signal is characterized in that it includes all the sound data from the plurality of camera devices 300, which is then transmitted to the sound decoder 252 and the amplifier 240.

In certain embodiments, an individual camera device 300 may be muted to stop the microphone 330 from capturing sound data. Another option includes the situation when the sound data has a volume less than a pre-determined level. In such a case, the camera processor 340 is further configured to nullify the sound data when generating the data packet 700 for reducing a transmission time of the data packet 700 from the individual camera device 300 to the base station 200.

In the first embodiment, the frame frequency of the first frame 810 and the second frame 820 may be synchronized. In such case, the camera devices 300 and the base station 200 each comprise a phase lock loop circuit configured to define a synchronized frequency for handling the data packets.

In the second embodiment, the frame frequency of the first frame 810 and the second frame 820 are not synchronized. In such case, the camera devices 300 and the base station 200 each comprise a phase lock loop circuit configured to define a non-synchronized frequency for handling the data packets. The information from the camera devices 300 may arrive randomly. The base station 200 is therefore configured to present updated information when a new content is received at a starting time of the second frame 820.

It is apparent that the description for the plurality camera devices 300 is also applicable to the case of other devices. Therefore, the communication using the data packets 700 is also processed similarly when a plurality of heterogeneous sources is used.

This illustrates the monitor system 100 having two or more camera devices 300 or other heterogeneous sources that is capable of outputting audio signals from the two or more camera devices 300 simultaneously. Particularly, the monitor system 100 can solve the problem commonly found in conventional baby monitor system with a split-screen. It will be apparent that variants of the above-disclosed and other features and functions, or alternatives thereof, may be combined into many other different systems or apparatuses. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

What is claimed is:

1. A monitor system for simultaneously monitoring one or more target subjects, the monitor system comprising:
    a plurality of camera devices arranged to capture video data and sound data of the one or more target subjects independently and simultaneously, wherein an individual camera device comprises a camera processor configured to generate a data packet; and
    a base station configured to receive the video data and the sound data from the plurality of camera devices, and present the video data and the sound data uninterruptedly,
    wherein:
        the base station comprises a display panel partitioned into a plurality of regions for displaying multiple views simultaneously using a split-screen technique;
        the base station outputs an audio signal by combining the sound data from the plurality of camera devices into a single audio signal;
        the base processor is configured to receive the data packets from the plurality of camera devices and process the data packets sequentially and continuously; and
        the camera processor is further configured to nullify the sound data when generating the data packet if the individual camera device is muted or the sound data has a volume less than a pre-determined level for reducing a transmission time of the data packet from the individual camera device to the base station.

2. The monitor system of claim 1, wherein the base station comprises:
    an amplifier; and
    a base processor configured to:
        decode the sound data and the video data;
        add or combine the sound data from the plurality of camera devices to obtain the single audio signal; and
        transmit the single audio signal to the amplifier.

3. The monitor system of claim 2, wherein the individual camera device further comprises:
    a sound capture circuitry comprising a microphone for acquiring the sound data of the target subject; and
    a video capture circuitry provided in a camera assembly for acquiring the video data of the target subject;
    wherein the data packet comprises a header and a payload data, and wherein the header comprises a pairing identity (ID) for identifying the individual camera device, and wherein the payload data comprises the sound data, the video data, and a temperature reading captured by the individual camera device.

4. The monitor system of claim 3, wherein the camera processor is further configured to scale down the video data before generating the data packet for reducing a transmission time of the data packet from the individual camera device to the base station.

5. The monitor system of claim 3, wherein the camera assembly comprises a sensor module, one or more optical elements, one or more infrared (IR) light-emitting diodes (LEDs), and a photosensitive diode.

6. The monitor system of claim 2, wherein the sound data is encoded using a μ-Law algorithm or an A-Law algorithm.

7. The monitor system of claim 2, wherein the video data is encoded using an advanced video coding (AVC) codec.

8. The monitor system of claim 1, wherein the plurality of camera devices transmits the data packet to the base station during a first frame, and the base station presents information from the data packet during a second frame.

9. The monitor system of claim 1, wherein the plurality of camera devices is wirelessly connected to the base station using radio frequency (RF) signals.

10. A monitor system for simultaneously monitoring one or more target subjects using a series of time frames, the series of time frames being pre-determined in frame periods, the monitor system comprising:
    a plurality of heterogeneous sources arranged to monitor the one or more target subjects independently and simultaneously, and transmit a data packet to the base station during a first frame of the series of time frames; and
    a base station configured to receive the data packet from the plurality of heterogeneous sources, and presents information from the data packet during a second frame of the series of time frames,
    wherein:
        the data packet comprises a header for identifying an individual heterogeneous source and a payload data obtained by the individual heterogeneous source;
        the payload data from the plurality of heterogeneous sources are displayed or output from the base station during the second frame simultaneously; and
        the plurality of heterogeneous sources and the base station each comprise a phase lock loop circuit configured to define a synchronized frequency for handling the data packet.

11. The monitor system of claim 10, wherein the plurality of heterogeneous sources comprises one or more detectors selected from the group consisting of a camera device, a heartbeat sensor, a proximity sensor, a temperature sensor, and a hall-effect sensor, wherein:
    the temperature sensor and the heat beat sensor are configured to obtain vitals of the target subject; and the hall-effect sensor is installed on a children's safety product for confirming whether the children's safety product is properly secured or closed.

12. The monitor system of claim 10, wherein the individual heterogeneous source comprises a processor configured to generate the data packet, wherein the header comprises a pairing identity (ID).

13. The monitor system of claim 10, wherein the base station is capable of simultaneously and independently presenting multiple views from the plurality of heterogeneous sources using a split-screen technique.

14. The monitor system of claim 10, wherein the base station is capable of producing an audio output from sound data captured from the plurality of heterogeneous sources.

15. The monitor system of claim 10, wherein the plurality of heterogeneous sources is wirelessly connected to the base station using radio frequency (RF) signals.

16. A monitor system for simultaneously monitoring one or more target subjects using a series of time frames, the series of time frames being pre-determined in frame periods, the monitor system comprising:
    a plurality of heterogeneous sources arranged to monitor the one or more target subjects independently and simultaneously, and transmit a data packet to the base station during a first frame of the series of time frames; and
    a base station configured to receive the data packet from the plurality of heterogeneous sources, and presents information from the data packet during a second frame of the series of time frames,
    wherein:
        the data packet comprises a header for identifying an individual heterogeneous source and a payload data obtained by the individual heterogeneous source;
        the payload data from the plurality of heterogeneous sources are displayed or output from the base station during the second frame simultaneously; and
        the plurality of heterogeneous sources and the base station each comprise a phase lock loop circuit configured to define a non-synchronized frequency for handling the data packet, and wherein the base station is configured to present updated information when a new content is received at a starting time of the second frame.

17. The monitor system of claim 16, wherein the plurality of heterogeneous sources comprises one or more detectors selected from the group consisting of a camera device, a heartbeat sensor, a proximity sensor, a temperature sensor, and a hall-effect sensor, wherein:
    the temperature sensor and the heat beat sensor are configured to obtain vitals of the target subject; and
    the hall-effect sensor is installed on a children's safety product for confirming whether the children's safety product is properly secured or closed.

18. The monitor system of claim 16, wherein the individual heterogeneous source comprises a processor configured to generate the data packet, wherein the header comprises a pairing identity (ID).

19. The monitor system of claim 16, wherein the base station is capable of simultaneously and independently presenting multiple views from the plurality of heterogeneous sources using a split-screen technique.

20. The monitor system of claim 16, wherein the base station is capable of producing an audio output from sound data captured from the plurality of heterogeneous sources.

21. The monitor system of claim 16, wherein the plurality of heterogeneous sources is wirelessly connected to the base station using radio frequency (RF) signals.

\* \* \* \* \*